United States Patent [19]
Gruenwald et al.

[11] Patent Number: 5,858,682
[45] Date of Patent: Jan. 12, 1999

[54] E2A/PBX1 FUSION PROTEIN SPECIFIC MONOCLONAL ANTIBODIES

[75] Inventors: Stefan Gruenwald, Encinitas; Bi-Ching Sang, San Diego; Craig Monell, La Jolla, all of Calif.

[73] Assignee: Pharmingen, San Diego, Calif.

[21] Appl. No.: 691,997

[22] Filed: Aug. 2, 1996

[51] Int. Cl.$^6$ .................. G01N 33/567; G01N 33/53; G01N 33/543; C07K 16/00
[52] U.S. Cl. .................. 435/7.1; 435/7.9; 435/7.91; 435/7.92; 435/7.93; 435/7.94; 435/7.95; 435/325; 435/326; 435/330; 435/331; 435/344.1; 435/810; 435/960; 435/975; 435/69.6; 435/69.7; 436/518; 436/547; 436/548; 436/64; 436/813; 530/327; 530/328; 530/329; 530/330; 530/387.3; 530/387.7; 530/387.9; 530/388.1; 530/388.73; 530/808; 530/809; 530/867; 935/89; 935/93
[58] Field of Search .................. 935/89, 93; 435/7.1, 435/7.9–7.95, 240.1, 240.26, 240.27, 240.2, 240.25, 240.23, 810, 960, 975, 69.6, 69.7, 325, 326, 330, 331, 344.1; 436/578, 547, 548, 813, 64; 530/327–330, 387.3, 387.7, 387.9, 388.1, 388.73, 808, 809, 867

[56] References Cited

U.S. PATENT DOCUMENTS 5,328,837  7/1994  Godowski et al. .................. 435/69.4

FOREIGN PATENT DOCUMENTS 13172  9/1991  WIPO.

OTHER PUBLICATIONS

Antibodies, eds. Harlow and Lane, p. 76, 1988.
Berendes et al., "Specific immunologic recognition of the tumor–specific E2A–PBX1 fusion–point antigen in t(1;19)–positive pre–B cells," *Leukemia* 9:1321–1327 (1995).
Carroll et al., "Pre–B Cell Leukemia Associated with Chromosome Translocation 1;19," *Blood* 63:761–764 (1984).
Dedera et al., "Chimeric Homeobox Gene E2A–PBX1 Induces Proliferation, Apoptosis, and Malignant Lymphomas in Transgenic Mice," *Cell* 74:833–843 (1993).
Henthorn et al., "Two Distinct Transcription Factors That Bind the Immunoglobulin Enhancer μE5/κE2 Motif," *Science* 247:467–470 (1990).
Hu et al., "HEB, a Helix–Loop–Helix Protein Relates to E2A and ITF2 That Can Modulate the DNA–Binding Ability of Myogenic Regulatory Factors," *Molecular Cell Biology* 12:1013–1042 (1992).
Hunger et al., "The t(1;19) (q23;p13) Results in Consistent Fusion of E2A and PBX1 Coding Sequences in Acute Lymphoblastic Leukemias," *Blood* 77:687–693 (1991).
Izraeli et al., "Unexpected Heterogeneity in E2A/PBX1 Fusion Messenger RNA Detected by the Polymerase Chain Reaction in Pediatric Patients with Acute Lymnphoblastic Leukemia," *Blood* 80:1413–1417 (1992).

Jacobs et al., "E2A Expression, Nuclear Localization, and In Vitro Formation of DNA–and Non–DNA–Binding Species during B–Cell Development," *Molecular Cell Biology* 13:7321–7333 (1993).
Kadesch, "Helix–loop–helix proteins in the regulation of immunoglobulin gene transcription," *Immunology Today* 13:31–36 (1992).
Kamps et al., "The human t(1;19) translocation in pre–B ALL produces multiple nuclear E2A–PBX1 fusion proteins with differing transforming potentials," *Gene & Development* 5:358–368 (1991).
Kamps et al., "A New Homeobox Gene Contributes the DNA Binding Domain of the t(1;19) Translocation Protein in Pre–B ALL," *Cell* 60:547–555 (1990).
LeBrun et al., "Fusion with E2A alters the transcriptional properties of the homeodomain protein PBX1 in t(1;19) leukemias," *Oncogene* 9:1641–1647 (1994).
Lu et al., "Both Pbx1 and E2A–Pbx1 Bind the DNA Motif ATCAATCAA Cooperatively with the Products of Multiple Murine Hox Genes, Some of Which are Themselves Oncogenes," *Molecular Cell Biology* 15:3786–3795 (1995).
Monica et al., "Transformation Properties of the E2a–Pbx1 Chimeric Oncoprotein: Fusion with E2a is Essential, but the Pbx1 Homeodomain is Dispensible," *Molecular Cell Biology* 14:8304–8314 (1994).
Murre et al., "Structure and function of the helix–loop–helix proteins," *Biochem. Biophys. Acta* 1218:129–135 (1994).
Nelson et al., "Pan: a transcriptional regulator that binds chymotrypsin, insulin, and AP–4 enhancer motifs," *Gene & Development* 4:1035–1043 (1990).
Nourse et al., "Chromosomal Translocation t(1;19) Results in Synthesis of a Homeobox Fusion mRNA That Encodes for a Potential Chimeric Transcription Factor," *Cell* 60:535–545 (1990).
Numata et al., "New E2A/PBX1 Fusion Transcript in a Patient with t(1;19)(q23;p13) Acute Lymphoblastic Leukemia," *Leukemia* 7:1441–1444 (1993).
Ohno et al., "Acute Lymphoblastic Leukemia Associated with a t(1;19)(q23;p13) in an Adult," *Internal Medicine* 32:584–587 (1993).
Privitera et al., "Molecular Variants of the 1;19 Chromosomal Translocation in Pediatric Acute Lymphoblastic Leukemia (ALL)," *Leukemia* 8:554–559 (1994).
Van Dijk et al. "Pbx1 is converted into a transcriptional activator upon acquiring the N–terminal region of the E2A in pre–B–cell acute lymphobloastoid leukemia," *Proc. Natl. Acad. Sci. USA* 90:6061–6065 (1993).
Williams et al., "New Chromosomal Translocations Correlate with Specific Immunophenotypes of Childhood Acute Lymphoblastic Leukemia," *Cell* 36:101–109 (1984).

Primary Examiner—Sheela Huff
Attorney, Agent, or Firm—Lyon & Lyon LLP

[57] ABSTRACT

A monoclonal antibody which specifically binds with an E2A/pbx1 fusion epitope.

34 Claims, 4 Drawing Sheets

FIG. 2A.

```
              10         20         30         40         50
pbx1    1  MDEQPRLMHS HAGVGMAGHP -GLSQHLQDG AG----GTEGE ---------G   50
pbx3    1  MDDQSRMLQT LAGVNLAGHS VQGGMALPPP PHGHEGADGD ----------   50
pbx2    1  MDE--RLLGP PP-PGGGRGG LGLVSGEPGG PGEPPGG-GD PGGGSGGVPG   50

60         70         80         90        100
pbx1   51  GR-KQDIGDI LQQIMTITDQ SLDEAQARKH ALNCHRMKPA LFNVLCEIKE  100
pbx3   51  GR-KQDIGDI LHQIMTITDQ SLDEAQAKKH ALNCHRMKPA LFSVLCEIKE  100
pbx2   51  GRGKQDIGDI LQQIMTITDQ SLDEAQAKKH ALNCHRMKPA LFSVLCEIKE  100

110        120        130        140        150
pbx1  101  KTVLSIRGAQ EEEPTDPQLM RLDNMLLAEG VAGPEKGGGS AAAAAAAAAS  150
pbx3  101  KTGLSIRGAQ EEDPPDPQLM RLDNMLLAEG VSGPEKGGGS AAAAAAAAAS  150
pbx2  101  KTGLSIRSSQ EEEPVDPQLM RLDNMLLAEG VAGPEKGGGS AAAAAAAAAS  150

160        170        180        190        200
pbx1  151  GGAGS-DNSV EHSDYRAKLS QIRQIYHTEL EKYEQACNEF TTHVMNLLRE  200
pbx3  151  GGS-S-DNSI EHSDYRAKLT QIRQIYHTEL EKYEQACNEF TTHVMNLLRE  200
pbx2  151  GGGVSPDNSI EHSDYRSKLA QIRHIYHSEL EKYEQACNEF TTHVMNLLRE  200

210        220        230        240        250
pbx1  201  QSRTRPISPK EIERMVSIIH RKFSSIQMQL KQSTCEAVMI LRSRFLDARR  250
pbx3  201  QSRTRPISPK EIERMVGIIH RKFSSIQMQL KQSTCEAVMI LRSRFLDARR  250
pbx2  201  QSRTRPVAPK EMERMVSIIH RKFSAIQMQL KQSTCEAVMI LRSRFLDARR  250

260        270        280        290        300
pbx1  251  KRRNFNKQAT EILNEYFYSH LSNPYPSEEA KEELAKKCGI TVSQVSNWFG  300
```

```
pbx3  251  KRRNFSKQAT  EILNEYFYSH  LSNPYPSEEA  KEELAKKCSI  TVSQVSNWFG  300
pbx2  251  KRRNFSKQAT  EVLNEYFYSH  LSNPYPSEEA  KEELAKKCGI  TVSQVSNWFG  300

310         320         330         340         350
pbx1  301  NKRIRYKKNI  GKFQEEANIY  AAKTAVTATN  -VSAHGS--Q  ANSPSTPNSA  350
pbx3  301  NKRIRYKKNI  GKFQEEANLY  AAKTAVTAAH  AVAAAVQNNQ  TNSPTTPNS-  350
pbx2  301  NKRIRYKKNI  GKFQEEANIY  AVKTAVSVTQ  GGHS-----R  TSSPTPPSSA  350

360         370         380         390         400
pbx1  351  GSSSSFNMSN  SGDLFMSVQS  LNGDSYQGAQ  VGANVQSQVD  TLRHVISQTG  400
pbx3  351  GSSGSFNLPN  SGDMFMNMQS  LNGDSYQGSQ  VGANVQSQVD  TLRHVINQTG  400
pbx2  351  GSGGSFNLSG  SGDMFLGMPG  LNGDSYSASQ  V-------E  SLRHSMGP-G  400

410         420         430         440         450
pbx1  401  GYSDGLAASQ  MYSPQGISAN  GGWQDATTPS  SVTSPTEGPG  SVHSDTSN..  450
pbx3  401  GYSDGLGGNS  LYSPHNLNAN  GGWQDATTPS  SVTSPTEGPG  SVHSDTSN..  450
pbx2  401  GYGDNLGGGQ  MYSPREMRAN  GSWQEAVTPS  SVTSPTEGPG  SVHSDTSN..  450
```

FIG. 2B.

E2A/PBX1 FUSION PROTEIN SPECIFIC MONOCLONAL ANTIBODIES

FIELD OF THE INVENTION

This invention relates to the field of immunology and diagnostics.

BACKGROUND OF THE INVENTION

The t(1;19)(q23,p13.3) chromosomal translocation creates a fusion protein named E2A/pbxl (Kamps M P, et al., *Cell* 60:547–555, 1990; Nourse J, et al. *Cell*, 60:535–545, 1990). This protein is detected in 25% of childhood pre-B acute lymphoblastic leukemias (ALL) (Carroll A J, et al. *Blood*, 63:761–764, 1984; Williams D, et al. *Cell*, 36:101–109, 1984) and has also been reported to be present in some cases of adult ALL (Ohno H, et al. *Internal Medicine*, 32:584–587, 1993).

In normal B cells, the E2A gene encodes 3 transcription factors E12, E47, and ITF-1/E2-5 by alternative splicing of a common messenger RNA (Hanthom P, *Science* 1990; 247:467–470; Nelson C, et al. *Genes Dev* 4:1035–1043, 1990). These proteins belong to the basic helix-loop-helix (bHLH) family of transcription factors. It has been shown that this family of proteins forms homo and hetero dimers by interaction through their bHLH motifs. These complexes form tissue-specific transcriptional regulatory factors involved in various developmental pathways (Kadesch T., *Immuno Today* 13:31–36, 1992; Hu L Olson EN, et al. *Mol Cell Biol*, 12:1031–1042, 1992; Murre C, *Biochem Biophys Acta*, 1218:129–135, 1994). Pbx1 belongs to a homeobox gene family whose members are pbx1, pbx2, and pbx3. Pbx1 is expressed in all tissues except B- and T-cell lineages. The homeodomain of pbx1 binds to the sequence ATCAATCAA (VanDijk M A, et al. *Proc Natl Acad Sci, USA* 90:6061–6065, 1993; Ubrun D, et al. *Oncogene* 9:1641–1647, 1994; Lu Q Knoepfler P S, et al. *Mol Cell Biol* 15:3786–3795, 1995). Based on the high degree of homology of pbx1 homeodomain to yeast a1 and a2, two transcriptional repressors, it has been suggested that pbx1 might act similarly as a transcriptional repressor in mammalian cells (Kamps M P, et al., *Cell* 60:547–555, 1990; Nourse J, et al. *Cell*, 60:535–545, 1990).

The E2A/pbxl fusion protein consists of an N-terminal portion of 483 amino acids of the E2A protein fused with 342 or 259 amino acids from the C-terminus of pbx1 (Kamps M P, et al., *Cell* 60:547–555, 1990; Nourse J, et al. *Cell*, 60:535–545, 1990). The different sizes of the pbx1 portion results from a splice variant of pbx1 which deletes a region of the pbx1 c-terminus to the homeobox domain. The junction in both forms is identical (Kamps M P, et al., *Genes & Dev.* 5:358–365, 1991). The bHLH and DNA binding domains of E2A are deleted as a result of the t(1;19) translocation, but the activation domain of E2A is still retained in the fusion protein. It has been shown that a reporter gene construct containing pbx1 homeodomain DNA binding sequence is transactivated by E2A/pbxl but not by pbx1 (VanDijk M A, et al. *Proc Natl Acad Sci, USA* 90:6061–6065, 1993). This leads to the postulation that the spacially and temporally incorrect activation of pbx1 responsive genes contributes to the pre-B-ALL phenotype (VanDijk M A, et al. *Proc Natl Acad Sci, USA* 90:6061–6065, 1993; Ubrun D, et al. *Oncogene* 9:1641–1647, 1994; Lu Q Knoepfler P S, et al. *Mol Cell Biol* 15:3786–3795, 1995). Transgenic mice studies, however, show that the E2A region is essential and the pbx1 homeodomain is dispensable for the development of malignant lymphomas (Monica K, et al. *Mol Cell Biol* 14:8304–8314, 1994). This finding suggests that the oncogenesis might be due to interactions between cellular proteins with E2A/pbx1 instead of homeodomain-DNA interactions. Little is known about the oncogenic mechanism conferred by the E2A/pbx1 chimeric protein. Although leukemic patients carrying the t(1;19) translocation are associated with a poorer prognosis, it is not known how this genetic abnormality confers such aggressive behavior. Over 85% of ALL patients with t(1;19) expressing E2A/pbx1 transcripts exhibit the same breakpoint (Hunger S P, et al. *Blood* 77:687–692, 1991; Izraeli S, et al. *Blood* 80:1413–1417, 1992).

Berendes et al., *Leukemia*, 9:1321–1327, 1995, disclose a polyclonal antiserum which was generated using the fusion-point E2A-pbx1 peptide LSRPPDSYSYLSIR.

To date, attempts to raise monoclonal antibodies to the E2A/pbx1 fusion protein have failed to result in monoclonal antibodies immunospecific for the E2A/pbx1 fusion proteins alone. It has been found that an antigenic peptide spanning the junction region, which includes the amino acid sequence PDSYS (SEQ. ID. NO. 1), contributed from the E2A protein, does not result in the production of fusion specific monoclonal antibodies.

SUMMARY OF THE INVENTION

The present invention provides monoclonal antibodies that are highly specific for the junction region of the E2A/pbx1 chimeric protein associated with ALL. This invention also provides a method for producing the new monoclonal antibodies, novel hybrid cell lines for the production of such monoclonal antibodies, and diagnostic methods for using monoclonal antibodies as reagents to detect ALL. These antibodies do not interact with E2A nor pbx1 alone, but specifically recognize the E2A/pbx1 chimeric protein. An especially important property of these antibodies is their ability to distinguish t(1;19)-positive from t(1;19)-negative cells by recognizing the aberrant gene product directly in immunohistochemical staining and flow cytometric analysis. These antibodies have been used to specifically stain cells containing the t(1;19) translocation by immunoperoxidase staining and in immunofluorescence both for microscopy as well as flow cytometry. Therefore these reagents will have a diagnostic potential as the breakpoint and fusion of E2A and pbx1 has been detected in most of the t(1;19) containing leukemias. For example, the G289-781 monoclonal antibody when tested on four clinical samples was able to distinguish t(1;19) positive from negative ALL cells.

The present invention also encompasses the production and use of monoclonal antibodies specific for pbx1 as a diagnostic reagent for pre-B cell acute lymphoblastic leukemia (ALL) arising from the t(1;19) (q23,p13.3) chromosomal translocation. The protein pbx1 is expressed in all tissues except B and T cell lineages. The only known instances in which sequences unique to pbx1 are seen in cell of the B lineage are cases in which they are expressed in a fusion protein with E2A resulting from the t(1; 19)(q23, p13.3) chromosomal translocation (Kamps, M. P., et al. *Cell* 60:547–555, 1990; Nourse et al. *Cell* 60:535–545, 1990). Therefore, in reacting to cells of the B lineage, the mAbs to pbx1 specifically indicate the presence of the translocation and are useful in detecting and monitoring the resultant ALL. Combining monoclonal antibodies specific for pbx1 with B and T cell lineage markers in multicolor flow cytometry allow selection of the cells carrying the translocation.

Several t(1;19) containing leukemias have been reported in which the fusion between E2A and pbx1 occurs at a different point (Numata S-L Kato K, et al. *Leukemia* 7:1441–1444, 1993; Privitera E, *Leukemia* 8:554–559, 1994). Izraeli et al. reported 3 out of 21 cases have an E2A/pbx1 transcript with a variant junction containing a 27 base pair of an in-frame insertion (Izraeli S, et al. *Blood* 80:1413–1417, 1992). Monoclonal antibodies have also been developed that are specific for this variant junction and may prove useful for the identification of subclasses of ALL.

The constant and variant junctions specific antibodies and antibodies to pbx1 could be used for aiding clinical diagnosis, subclassification of ALL and predicting prognosis of patients harboring genetic abnormalities associated with ALL. They would allow the identification of high risk patients who might benefit from intensified initial chemotherapeutic regimens, and for detection of minimal residual disease and early relapse. In addition to their potential clinical utility the monoclonal antibodies of the present invention should aid in the understand the pathogenic mechanism(s) of the E2A/pbx1 chimeric protein in oncogenesis (leukemia).

Recently, the oncogenicity of chimeric E2A/pbx1 polypeptides has been demonstrated by incorporating the open reading frame of E2A/pbx1 into a retrovirus construct and using it to infect normal mouse marrow progenitor cells (Dedera, D A, et al. *Cell*, 74:833, 1993). The cells were used in a bone marrow transplantation experiment to reconstitute the hematopoietic compartments of lethally irradiated mice. After 3 to 8 months, reconstituted mice developed acute myeloid leukemias that expressed high levels of E2A/pbx1 and were readily transmissible to immunocompetent mice. Most acute myeloid leukemias also grew as granulocytic sarcomas and exhibited some neutrophilic differentiation. In transgenic mice, ectopic expression of E2A/pbx1 induced both malignant lymphomas and apoptosis. These results demonstrate a causative role for E2A/pbx1 in ALL and indicate that the oncogenic potential of E2A/pbx1 is not limited to pre-B malignancies. Thus the monoclonal antibodies of the present invention may be applicable to the diagnosis of other disease states.

Optimal panels of mAbs(E2A/pbx1 junction and pbx1) for each application will be selected. These will serve as basis for a clinical kit development for childhood pre-B leukemia. Such a diagnostic kit will allow clinical reference laboratories to screen a heterogeneous population of cells from blood or bone marrow for the presence of the E2A/pbx1 fusion protein resulting in the fast and reliable detection of t(1;19) bearing leukemia cells.

In addition to the already discussed specific advantages offered by the monoclonal antibodies of the present invention, monoclonal antibodies in general have significant advantages over conventional antisera with respect to specificity and availability.

Thus, in a first aspect the invention features a monoclonal antibody which specifically binds with an E2A/pbx1 fusion epitope. Such a monoclonal antibody does not specifically bind with an E2A peptide (PDSYS) (SEQ. ID. NO. 1) or an pbx1 peptide(VLSIRGAQ) (SEQ. ID. NO. 2), but does bind to the epitope produced from the fusion gene formed between E2A and pbx1.

In a second aspect, the invention features a monoclonal antibody produced using an immunogenic fusion peptide comprising the sequence SYSVLS (SEQ. ID. NO. 3).

In preferred embodiments the immunogenic fusion peptide comprises the amino acid sequence SYSVLSIRGAQEEC (SEQ. ID. NO. 4); the immunogenic fusion peptide is the amino acid sequence SYSVLSIRGAQEEC.

In a further aspect, the invention features a monoclonal antibody produced using an immunogenic fusion peptide comprising the sequence YSVLS (SEQ. ID. NO. 11).

The invention also features a monoclonal antibody produced using an immunogenic fusion peptide comprising the sequence SVLS (SEQ. ID. NO. 12).

In a third aspect, the invention features a method of producing a monoclonal antibody which is immunospecific for a E2A/pbx1 fusion epitope comprising the steps of: immunizing a mouse with a fusion peptide comprising the sequence SYSVLS (SEQ. ID. NO. 3); producing a plurality of hybridoma cells from the mouse; and; identifying among the plurality of hybridoma cell lines those which produce a monoclonal antibody which specifically reacts with an E2A/pbx1 fusion protein.

In preferred embodiments the fusion peptide comprises the sequence SYSVLSIRGAQEEC (SEQ ID. NO. 4); the fusion peptide has the sequence SYSVLSIRGAQEEC.

In a fourth aspect, the invention features culturing a hybridoma cell line that produces a monoclonal antibody produced by the method of claim 5.

In a fifth aspect, the invention features a hybridoma cell line which produces a monoclonal antibody which specifically reacts with an E2A/pbx1 fusion protein.

In a preferred embodiment the hybridoma cell line produces a monoclonal antibody which was made using a fusion peptide comprising the sequence SYSVLS (SEQ ID. NO. 3).

In a sixth aspect, the invention features a method for detecting a subset of patients having acute lymphoblastic leukemia, comprising the steps of: contacting a sample obtained from a subject suspected of having acute lymphoblastic leukemia with a monoclonal antibody specifically reactive with an E2A/pbx1 epitope so as to form a detectable complex between the monoclonal antibody and an E2A/pbx1 fusion protein present in the sample; and detecting the presence of the complex as an indication of acute lymphoblastic leukemia in a subset of patients.

In preferred embodiments, the monoclonal antibody is produced using a peptide comprising the sequence SYSVLS (SEQ. ID. NO. 3); the monoclonal antibody is produced using a peptide comprising the sequence SYSVLSIRGAQEEC (SEQ. ID. NO. 4); the monoclonal antibody is produced using a peptide with the sequence SYSVLSIRGAQEEC.

In a seventh aspect, the invention features a method for detecting a subset of patients having acute lymphoblastic leukemia, comprising the steps of: individually contacting a sample obtained from a subject suspected of having acute lymphoblastic leukemia with each member of a panel of monoclonal antibodies specifically reactive with an E2A/pbx1 epitope so as to allow a detectable complex to form between a member of the panel of monoclonal antibodies and an E2A/pbx1 fusion protein present in the sample; detecting the presence or absence of complexes produced from the panel of monoclonal antibodies as an indication of the presence of acute lymphoblastic leukemia in the subset of patients.

In an eighth aspect, the invention features a kit for detecting acute lymphoblastic leukemia, the kit comprising one or more monoclonal antibody compositions comprising one or more monoclonal antibodies produced with a fusion peptide comprising the sequence SYSVLS (SEQ. ID. NO. 3) and which specifically reacts with an E2A/pbx1 fusion epitope or E2A/pbx1 fusion protein.

In a preferred embodiment the kit further comprises reagents useful for detecting one or more of the monoclonal antibodies, such as secondary antibodies.

In a ninth aspect, the invention features a monoclonal antibody which specifically binds with an E2A/pbx1 fusion splice variant epitope.

In preferred embodiments the monoclonal antibody is produced using an immunogenic fusion peptide comprising the sequence DSYSDESV (SEQ. ID. NO. 5); the monoclonal antibody is produced using an immunogenic fusion peptide with the sequence DSYSDESV.

In a tenth aspect, the invention features a hybridoma cell line which produces a monoclonal antibody which was produced using a fusion peptide comprising the sequence DSYSDESV (SEQ. ID. NO. 5) and which specifically binds with an E2A/pbx1 fusion splice variant epitope In an eleventh aspect, the invention features a method of producing a monoclonal antibody which is immunospecific for a E2A/pbx1 fusion splice variant epitope comprising the steps of: immunizing a mouse with a fusion peptide comprising the sequence DSYSDESV (SEQ. ID. NO. 5); producing a plurality of hybridoma cells from the mouse; and identifying among the plurality of hybridoma cell lines those which produce a monoclonal antibody which specifically reacts with an E2A/pbx1 fusion protein.

In a twelfth aspect, the invention features monoclonal antibodies and monoclonal antibody fragments which are specific for an E2A/pbx1 fusion epitope produced using recombinant DNA techniques.

In preferred embodiments the monoclonal antibody fragments are Fv or Fab.

In a thirteenth aspect, the invention features a monoclonal antibody which specifically binds to pbx1 protein.

In a fourteenth aspect, the invention features a monoclonal antibody which specifically binds to pbx1 protein produced using an immunogenic peptide comprising three or more contiguous amino acids selected from the sequence ATNVSAHGSQANSP (SEQ. ID. NO. 6).

In a fifteenth aspect, the invention features a method of producing a monoclonal antibody which is immunospecific for pbx1 comprising the steps of: immunizing a mouse with a peptide comprising three or more contiguous amino acids selected from the sequence ATNVSAHGSQANSP (SEQ. ID. NO. 6); producing a plurality of hybridoma cells from the mouse; and identifying among the plurality of hybridoma cell lines those which produce a monoclonal antibody which specifically reacts with pbx1 protein.

In a sixteenth aspect, the invention features culturing a hybridoma cell line that produces a monoclonal antibody produced by the method of claim 26.

In a seventeenth aspect, the invention features a hybridoma cell line which produces a monoclonal antibody which specifically reacts with pbx1 protein.

In an eighteenth aspect, the invention features a method for detecting a subset of patients having acute lymphoblastic leukemia comprising the steps of: contacting a sample obtained from a subject suspected of having acute lymphoblastic leukemia with a monoclonal specific for a pan-B cell surface antigen or a monoclonal specific for a pan-T cell surface antigen, a monoclonal antibody specifically reactive with pbx1 so as to form a detectable complex between the monoclonal antibody and an E2A/pbx1 fusion protein present in the sample; and detecting the presence of the complex in cells of B or T cell lineage as an indication acute lymphoblastic leukemia in the subset of patients.

In a nineteenth aspect, the invention features a method for detecting a subset of patients having acute lymphoblastic leukemia, comprising the steps of contacting a sample obtained from a subject suspected of having acute lymphoblastic leukemia with a monoclonal antibody specific for a pan-B cell surface antigen or a monoclonal antibody specific for a pan-T cell surface antigen, individually contacting the sample with each member of a panel of monoclonal antibodies specifically reactive with pbx1 protein so as to allow a detectable complex to form between a member of the panel of monoclonal antibodies and an E2A/pbx1 fusion protein present in the sample; and detecting the presence or absence of said complexes produced from said panel of monoclonal antibodies in cells of B or T cell lineage as an indication of the presence of acute lymphoblastic leukemia in said subset of patients.

In a twentieth aspect, the invention features a kit for detecting acute lymphoblastic leukemia, the kit comprising one or more monoclonal antibody compositions comprising one or more monoclonal antibodies which specifically react with pbx1 and one or more monoclonal antibody compositions comprising one or more monoclonal antibodies which specifically react with a pan-B cell surface antigen or a pan-T cell surface antigen.

In a preferred embodiment, the kit further comprising reagents which detect one or more of the monoclonal antibodies.

In a twenty-first aspect, the invention features mAbs or mAb fragments which specifically bind pbx1 protein produced using recombinant DNA techniques.

In preferred embodiments the monoclonal antibody fragments are Fv or Fab.

BRIEF DESCRIPTION OF THE FIGURES

FIGS. 2A and 2B represent alignment of the amino acid sequences of pbx1, pbx2, and pbx3. Pbx1 specific regions past E2A junction are underlined (these are not conserved in either pbx2 or pbx3). The numbers are position numbers including the gaps after alignment.

DESCRIPTION OF THE PREFERRED EMBODIMENTS

Definitions

Figure 1A:
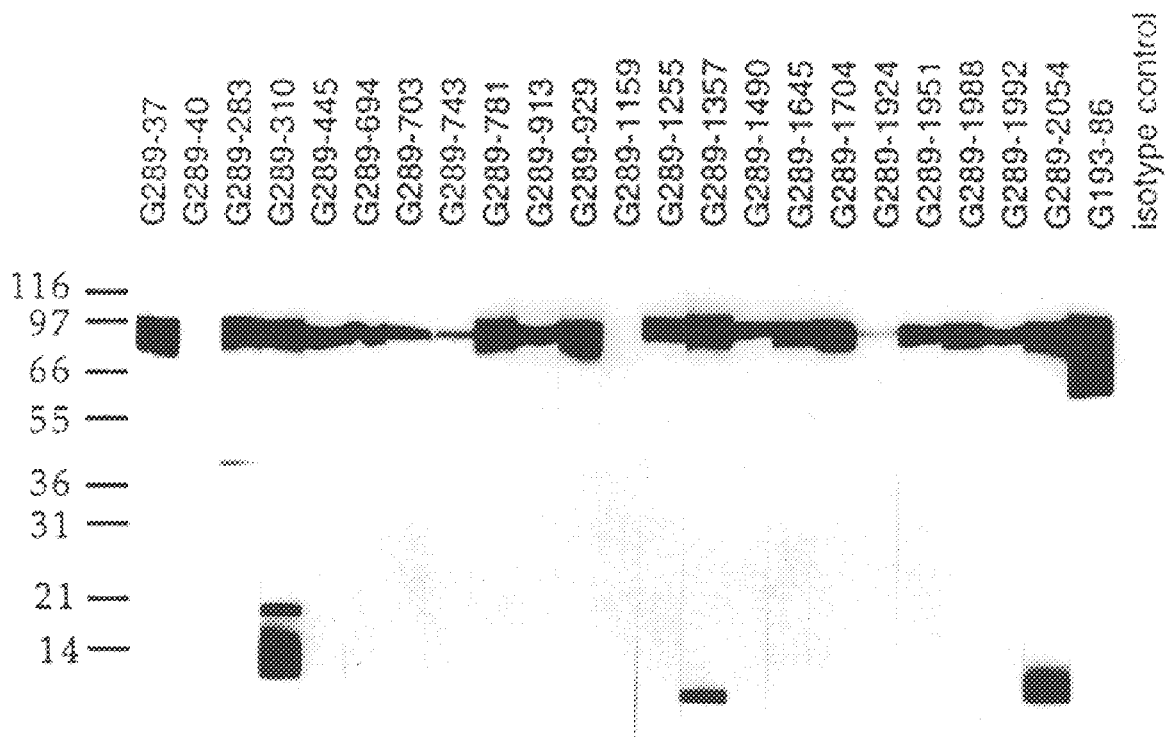
FIGS. 1(A–B) represents a western blot using monoclonal antibody clones obtained from fusion #G289. Total cell lysates from the E2A/pbx1 carrying line 697 (FIG. 1A) and the EBV transformed pre-B line Namalwa (FIG. 1B) were separated on 4–20% SDS PAGE and transferred to Immobilon-P membrane. Individual membrane strips were probed with various G289-clones, an E2A-specific G193-86 clone, or an isotype control mAb using ECL.

The term "antibody" in its various grammatical forms refers to a composition containing immunoglobulin molecules and/or immunologically active portions of immunoglobulin molecules, i.e., molecules that contain an antibody combining site or paratope.

The phrase "monoclonal antibody" (mAb) designates an antibody produced by clones of a single cell called a hybridoma that secretes but one kind of antibody molecule. The hybridoma cell is formed by fusing an antibody-producing cell and a myeloma or other self-perpetuating cell line. Such antibodies were first described by Kohler and Milstein, *Nature,* 256:495–497 (1975), which description is incorporated by reference. The phrase "monoclonal antibody" also includes antibodies which are produced using recombinant techniques, such as those described by Fuchs et al. *Cell Biophys,* 21:81–91, 1992; Burton et al. *Adv. Immunol,* 57:191–280, 1994; Crosby et al. *Methods Cell Biol.* 50:85–99, 1995; Ward, E. S. *Mol. Immunol.,* 32:147–56, 1995; Hayashi et al. *Gene,* 160:129–30, 1995; and Ward et al. *J. Immunol. Methods,* 189:73–82, 1996.

Monoclonal antibody compositions are contemplated by the present invention. A monoclonal antibody composition contains, within detectable limits, only one species of antibody combining site capable of effectively binding. Thus, for example, a monoclonal antibody composition of the present invention typically displays a single binding affinity for the E2A/pbx1 fusion protein even though it may contain antibodies capable of binding proteins other than the E2A/pbx1 fusion protein.

The phrase "monoclonal antibody" in its various grammatical forms refers to an antibody molecule containing composition having only one species of antibody combining site capable of immunoreacting with a particular epitope. A monoclonal antibody thus typically displays a single binding affinity for any epitope with which it immunoreacts. A monoclonal antibody may therefore contain an antibody molecule having a plurality of antibody combining sites, each immunospecific for a different epitope, e.g., a bispecific monoclonal antibody.

The word "antigen" has been used historically to designate an entity that is bound by an antibody, and also to designate the entity that induces the production of the antibody. More current usage limits the wearing of antigen to that entity bound by an antibody, the word "immunogen" is used for the entity that induces antibody production. Where an entity discussed herein is both immunogenic and antigenic, it will generally be termed an antigen.

"Antigenic determinant site" refers to the actual structural portion of the antigen that is immunologically bound by an antibody combining site. The term is also used interchangeably with "epitope".

Keyhole limpet hemocyanin (KLH) is a protein that is frequently utilized as a carrier for relatively low molecular weight, haptenic polypeptide conjugates used in the preparation of vaccines and other inocula. KLH is utilized as a carrier in immunogenic polypeptide conjugates because of its general T cell stimulatory and proliferative effects.

Other useful carriers are well known in the art, and are generally proteins themselves. Exemplary of such carriers are edestin, thyroglobulin, albumins such as bovine serum albumin (BSA) or human serum albumin (HSA), red blood cells such as sheep erythrocytes (SRBC), tetanus toxoid, cholera toxoid, hepatitis B virus core particles or immunogenic fragments thereof as well as polyamino acids such as poly (D-lysine: D-glutamic acid), and the like.

The choice of carrier is more dependent upon the ultimate use of the inoculum and is based upon criteria not particularly involved in the present invention. For example, a carrier that does not generate an untoward reaction in the particular mammal to be inoculated should be selected.

The labeling of proteinaceous receptor molecules is well-known in the art. The techniques of protein conjugation or coupling through activated functional groups are particularly applicable. See, for example, Aurameas, et al., *Scand. J. Immunol.,* Vol. 8, Suppl. 7:7–23 (1978) and U.S. Pat. No. 4,493,795 which is incorporated herein by reference. Methods for conjugating enzymes to proteins may be found in U.S. Pat. No. 3,791,932 and No. 3,839,153. In addition, site directed coupling reaction can be carried out so that the label does not substantially interfere with the immunoreaction of the second receptor with the E2A/pbx1 fusion protein or the pbx1 protein. See, for example, Rodwell et al., *Biotech.,* 3:889–894 (1985).

One or more additional amino acid residues may be added to the amino- or carboxy-termini of the synthetic polypeptide to assist in binding the synthetic polypeptide to a carrier to form a conjugate. Cysteine residues, usually added at the carboxy-terminus of the polypeptide, have been found to be particularly useful for forming conjugates via disulfide bonds, but other methods well-known in the art for preparing conjugates may be used.

The "effective amount" of antigenic polypeptide in a unit dose depends upon a number of factors. Included among those factors are the body weight of the animal immunized, the carrier when used, the adjuvant when used, and the number of inoculations desired to be used. Individual inoculations typically contain about 10 μg to about 500 mg of polypeptide per kg body weight exclusive of any carrier to which the polypeptide may be linked. Inoculation methods and amounts in rabbits for the purpose of raising antibodies are described below.

"Epitope" refers to that portion of a molecule that is specifically recognized by an antibody combining site. It also is referred to as the determinant or antigenic determinant.

As used herein, the term "synthetic polypeptide" means a chemically- as opposed to biologically-derived chain of amino acid residues that is free of naturally occurring proteins.

"Polypeptide" and "peptide" are terms used interchangeably herein to designate a linear series of no more than about 50 amino acid residues connected one to the other by peptide bonds between the alpha-amino and carboxy groups of adjacent residues. The terms polypeptide and peptide are meant to include both naturally occuring and synthetic molecules.

"Protein" is a term used herein to designate a linear series of greater than 50 amino acid residues connected one to the other as in a polypeptide.

A diagnostic system in kit form of the present invention includes, in an amount sufficient for at least one assay, a polypeptide, polypeptide admixture, antibody composition or monoclonal antibody composition of the present invention, as a packaged reagent. Instructions for use of the packaged reagent are also typically included.

As used herein, the term "package" refers to a solid matrix or material such as glass, plastic, paper, foil and the like capable of holding within fixed limits a polypeptide, antibody composition or monoclonal antibody composition of the present invention. Thus, for example, a package can be a glass vial used to contain milligram quantities of a contemplated polypeptide or it can be a microtiter plate well to which microgram quantities of a contemplated polypeptide have been operatively affixed, i.e., linked so as to be capable of being immunologically bound by an antibody.

"Instructions for use" typically include a tangible expression describing the reagent concentration or at least one assay method parameter such as the relative amounts of reagent and sample to be mixed, maintenance time periods for reagent/sample admixtures, temperature, buffer conditions and the like.

In preferred embodiments, a diagnostic system of the present invention further includes a label or indicating means capable of signaling the formation of a complex containing a polypeptide or antibody molecule of the present invention. Labels include both primary conjugates to the monoclonal antibodies of the present invention and secondary conjugates which bind to the monoclonal antibodies of the present invention such as labeled secondary antibodies.

The diagnostic systems can also include, preferably as a separate package, a specific binding agent. A "specific binding agent" is a molecular entity capable of selectively binding a reagent species of the present invention or a complex containing such a species, but is not itself a polypeptide or antibody molecule composition of the present invention. Exemplary specific binding agents are second antibody molecules, complement proteins or fragments thereof, S. aureus proteins A, and the like. Preferably the specific binding agent binds the reagent species when that species is present as part of a complex.

In preferred embodiments, the specific binding agent is labeled. However, when the diagnostic system includes a specific binding agent that is not labeled, the agent is typically used as an amplifying means or reagent. In these embodiments, the labeled specific binding agent is capable of specifically binding the amplifying means when the amplifying means is bound to a reagent species-containing complex.

Thus, in preferred embodiments, a polypeptide, antibody molecule composition or monoclonal antibody molecule composition of the present invention can be affixed to a solid matrix to form a solid support that comprises a package in the subject diagnostic systems.

The reagent is typically affixed to the solid matrix by adsorption from an aqueous medium although other modes of affixation, well known to those skilled in the art, can be used.

Useful solid matrices are also well known in the art. Such materials are water insoluble and include the cross-linked dextran available under the trademark SEPHADEX from Pharmacia Fine Chemicals (Piscataway, N.J.); agarose; beads of polystyrene about 1 micron to about 5 millimeters in diameter available from Abbott Laboratories of North Chicago, Ill.; polyvinyl chloride, polystyrene, cross-linked polyacrylamide, nitrocellulose- or nylon-based webs such as sheets, strips or paddles; or tubes, plates or the wells of microtiter plate such as those made from polystyrene or polyvinylchloride.

The reagent species, labeled specific binding agent or amplifying reagent of any diagnostic system described herein can be provided in solution, as a liquid dispersion or as a substantially dry powder, e.g., in lyophilized form. Where the indicating means is an enzyme, the enzyme's substrate can also be provided in a separate package of a system. A solid support such as the before-described microtiter plate and one or more buffers can also be included as separately packaged elements in this diagnostic assay system.

The packaging materials discussed herein in relation to diagnostic systems are those customarily utilized in diagnostic systems. Such materials include glass and plastic (e.g., polyethylene, polypropylene and polycarbonate) bottles, vials, plastic and plastic-foil laminated envelopes and the like.

Since the joining point of the E2A and pbx1 gene in all studied cases of t(1;19) translocations is highly precise and consistent, peptides which cover the fusion region of E2A and pbxl and a peptide (PDSYSDESVRSPGTFLSIRGC) (SEQ. ID. NO. 7) that covers the sequence of the junction between E2A and pbx1 of a splice variant were synthesized. Both peptides were crosslinked to keyhole limpet hemocyanin (KLH) and used as immunogens for Balb/c mice to develop monoclonal antibodies that are highly specific for the E2A/pbxl fusion protein.

In order to produce monoclonal antibodies that are specific to an epitope that covers the fusion region (junction) of E2A and pbxl and would selectively recognize the E2A/pbxl fusion protein, Balb/c mice were immunized with peptides spanning the junction region, such as: peptide 13 (PDSYSVLSIRGAQ) (SEQ. ID. NO. 8) and peptide 14 (SYSVLSIRGAQEEC) (SEQ. ID. NO. 4). The underlined part of the peptide belongs to the E2A protein whereas the bold part of the peptide is coded by pbx1. The C-terminal cysteine of peptide 14 was included to facilitate the chemical coupling to the carrier protein KLH.

Preparation of immunogen (a) Recombinant E2A/pbx1 junction protein: The Bst1 fragment (nt.386–1883) from pSKE2A/pbx1 was inserted into the SmaI site of the pGEX 4T-3 vector (Pharmacia). This recombinant E2A/pbx1 junction protein was expressed as a GST fusion protein in DH5 α E. coli and affinity-purified on glutathione-agarose beads as described previously (Guan K L, et al. Anal Biochem, 192:262–267, 1991).

(b) KLH-conjugated peptide: 2.1 mg of a E2A/pbx1-specific synthetic peptide (SYSVLSIRGAQEEC) (SEQ. ID. NO. 4), peptide 14 was dissolved in 500 µl of Phosphate-Buffered Saline (PBS, pH 7.3) containing 30% of DMSO. This peptide solution was added dropwise into 0.2 ml of 10 mg/ml of Maleimide activated Keyhole Limpet Hemocyanin (KLH)(PIERCE). The conjugation reaction was allowed to proceed for 2 hrs at room temperature. The conjugate was then dialyzed against PBS overnight.

Expression of recombinant pbx1 protein for screening

The pET21a plasmid containing the entire coding region of pbx1 was transformed into DH5 α E. coli. The recombinant 6xHis-tagged pbx1 protein was expressed after IPTG induction and purified using NTA beads (Qiagen) according to the manufacturer's instructions.

Immunization and development of monoclonal antibodies

Balb/c mice were immunized with antigen on days 1, 7, 14, 21, 28 and 3 days before fusion. The KLH-conjugated peptide 14 was used for the first 3 immunizations and recombinant E2A/pbx1 junction protein together with conjugated-peptide were used for the last 2 immunizations. Splenocytes from immunized mouse were then fused with NS-1 myeloma cells. Hybridoma supernatants were initially screened against KLH conjugated peptide by ELISA. The hybridomas whose antibodies recognized conjugated peptide were further screened by dot blot for specific reactivity against amino acid residues at the junction of the chimeric protein. Dot blotting was performed by spotting 100 ng of recombinant protein on nitrocellulose paper. The membrane was blocked with TBST-1% low fat milk for 1 hr at room temperature. The hybridoma supernatants were then incubated with the membranes, followed by alkaline phosphatase-conjugated goat anti-mouse Ia (PharMingen). The antibody reactivity was detected by using BCIP/NBT (Promega) substrate as the chromogen.

Western blotting

The B-cell line Namalwa, and the t(1;19)-carrying cell line 697 were cultured in Dulbecco modified Eagle medium (DMEM) containing 10% calf serum. Cells in the log phase were harvested and washed with PBS. Total cell lysate was prepared by adding SDS sample buffer to a cell pellet containing $1 \times 10^7$ cells/ml in lysis buffer, forced about 20 times through a 23½ G needle, and stored at −80° C. until use. Lysates were resolved by SDS-PAGE and transferred onto immobilon-P membranes (Millipore). Western blotting was performed by the standard method, using hybridoma supernatants, horse radish peroxidase-conjugated secondary antibodies, and developed by standard enhanced chemiluminescence (PIERCE). For peptide blocking, 10 µg of purified monoclonal antibodies were first incubated with 250 µg of peptide 14 for 1 hr at room temperature before applying them onto membrane.

Antibody purification 300 ml of junction-specific monoclonal antibody hybridoma supernatant was passed through 1.8 ml of protein G sepharose (Pharmacia) beads, washed with 10 beads volumes of 10 mM Tris•HCl, pH 7.5 and eluted off the column with 100 mM glycine, pH 3.0. The eluate was collected in 1 ml fractions containing 100 μl of 1M Tris•HCl, pH 7.5 to neutralize the acidity. The protein concentration of each fraction was measured by spectrophotometry at $OD_{280}$. The peak antibody containing fractions ($OD_{280}>0.3$) were combined and dialyzed against 10 mM Tris•HCl, 75 mM NaCl, pH 7.5.

Immunostaining

Immunofluorescence and immunohistochemical staining are the most commonly used techniques for detecting protein expression in tissue samples.

The cells were attached onto precoated slides (BioRad, Munchen, Germany), fixed with 2% formaldehyde (in PBS) for 20 min., washed once with PBS and permeabilized for 30 min. at room temperature with 0.1% saponin (in PBS) containing 1% hydrogen peroxide. In order to block non-specific staining the cells were then incubated in 1% BSA containing 0.1% saponin (in PBS) for 10 min. before incubating them overnight at 4° C. with purified antibody. The excess of unbound primary antibody was washed off and the cells then incubated for 30 min. with biotinylated donkey anti-mouse Ig (Jackson Immunoresearch Labs). After washing off excess unbound secondary antibody the cells were then incubated with horse-radish peroxidase (IWO) conjugated streptavidin reagent (Dako). The excess of unbound tertiary reagent was then removed and the cells were incubated in 0.1% 3,3' diaminobenzidine (DAB) solution containing 0.015% hydrogen peroxide and nickel chloride for 10 min. The cells were then washed extensively with water, counterstained with eosin, dehydrated in graded alcohol, cleared with xylene, and mounted with a coverslip for staining evaluation.

Positive-reacting mAbs are used for mixing experiments to assess the sensitivity and lower limit of detection. These should be useful for post-chemotherapy monitoring of minimal residual disease and early relapse detection. The simultaneous use of additional markers to surface epitopes commonly expressed in pre-B ALL including CD10 and CD19 in two-color and three-color combinations enhance the level of sensitivity of assays utilizing an E2A/pbx1 fusion mAb. Finally, the correlation of reactivity with t(1;19)-positive ALL can be assessed cytogenetically to aid in the further identification and charactertization of the disease state.

Flow cytometric analysis using an E2A/pbx1 junction-specific mAb

Cells were washed once with PBS containing 1% fetal calf serum and fixed with 4% paraformaldehyde for 1 hr at room temperature. The fixed cells were then washed twice with PBS, permeabalized with 100% methanol at −20° C. for 5 min, and washed with PBS. Approximately $5.5 \times 10^6$ cells were initially blocked with 1% BSA in PBS at room temperature for 20 min and then incubated with 1 μg of E2A/pbx1 junction-specific monoclonal antibodies for 30 min, washed, stained with FITC-conjugated goat anti-mouse Ig (2.5 μg/μl) for 30 min, washed, and fixed with 2% of formaldehyde. For peptide 14 blocking experiments, the junction-specific antibodies were incubated with 0.1 μg peptide 14 for 30 min at room temperature prior to their incubation with cells.

Flow cytometric analysis using a pbx1 specific mAb

A. Harvest Cells

Viable cell populations may be stained in plastic tubes or microwell plates. Cells should be protected from light throughout staining and storage.

B. Block Fc Receptors

Fc receptors on human cells may be pre-blocked with an excess of irrelevant purified Ig.

C. Stain Cell Surface Antigens

1. Stain $1 \times 10^6$ cells in 100 μl of Wash Buffer with 0.1–1 μg of a fluorochrome-conjugated monoclonal antibody specific for a pan-B cell surface antigen such as CD19, surface immunologulin, CD20, etc. or other lineage markers (30 min, 4° C.). Multi-color staining of different cell surface antigens can be done at this time for setting flow cytometric compensations.

2. Wash cells 2 times with Wash Buffer and pellet by centrifugation (250×g).

Wash Buffer: pH 7.4 PBS/0.1% NaN3/1% heat-inactivated fetal bovine serum

D. Fix Cells

Resuspend and fix cells with 100 μl of Fixation Buffer for 20 min at 4° C.

Fixation Buffer: Add 4% (w/v) paraformaldehyde to Dulbecco's PBS and warm in 50° C. water bath until the paraformaldehyde dissolves. Adjust buffer to pH 7.4–7.6.

E. Permeabilize Cells

Remove fixation buffer by centrifugation at 400×g for 10 min. Aspirate and wash once by re-suspending pellet in 30–40 ml of Wash Buffer. Centrifuge at 400×g for 10 min. Aspirate supernatant. Add 5 ml cold 0.25% Triton X-100, diluted in Wash Buffer, to the cell pellet. Vortex and incubate 5 min. Add wash buffer and centrifuge at 400×g for 10 min. Aspirate supernatant.

F. Stain with mAb to pbx-1 protein:

1. Add 0.1–1 μg of monoclonal antibodies to pbx1, or appropriate negative control. Incubate at 4° C. for 30 min in the dark.

2. Wash cells 2 times in Wash Buffer and pellet.

G. Analysis

Thoroughly resuspend cells in wash Buffer and analyze by flow cytometry. Set PMT voltage and compensation using cell surface staining controls. Set quadrant markers based on blocking controls.

Expression of recombinant E2A/pbx1 protein in insect cells

In order to assess the specificity of the obtained anti-peptide monoclonal antibodies, a full length E2A/pbx1 protein that contains the authentic E2A/pbx1 junction sequence was expressed in Baculovirus-infected insect cells. The E2A and pbx1 polypeptides were also expressed in insect cells and served as a negative control, since these do not contain the E2A/pbx1 junction sequence. The coding sequence of E2A/pbx1 was cut out of the Bluescript E2A/pbx1 construct and cloned into the pVL1393 vector. In order to express the variant junction form of E2A/pbx1, the current pBS E2A/pbx1 construct was mutated using standard PCR mutation technique. To this end, 4 PCR primers were designed, two of them are covering the mutated region and two of them covering flanking sites that contain a single-cutter restriction endonuclease site in the E2A/pbx1 sequence that allowed the PCR-mutated region to be cloned back into the E2A/pbx1 gene. Three independent PCR reactions were carried out, two of them resulting in the left and right-side fragment flanking the mutated E2A/pbx1 junction site. The third PCR reaction used these two PCR products and amplified the whole region including the two restriction sites for cloning the PCR product back into the gene. Recombinant Baculovirus transfer plasmids were co-transfected with linearized BaculoGold™ DNA (PharMingen) into Sf9 insect cells. Since linearized BaculoGold™ DNA contains a lethal deletion that has to be complemented by co-transfected plasmid DNA in order to recover viable virus particles, the use of BaculoGold™ DNA allows a positive selection for recombinant virus expressing the gene of interest in infected insect cells. This strategy allows recombination efficiencies of more than 99%. For recombinant protein production (E2A/pbx1, E2A and pbx1), insect cells were infected with recombinant Baculovirus particles at a multiplicity of infection (MOI) of 10, and the infected insect cells were harvested 3 days after infection. Harvested cells were lysed in Triton X-100-containing buffer and proteins were resolved using SDS-PAGE. All methods used to handle insect cells and express recombinant proteins in the Baculovirus Expression Vector System (BEVS) are according to protocols published in the Procedures and Methods Manual for the Baculovirus Expression Vector System (PharMingen).

Epitope mapping

The goal of the epitope mapping is to define the epitopes recognized by each obtained monoclonal antibody. A single mAb may not detect an alternatively spliced E2A/pbx1 fusion protein or a breakpoint variant of the t(1;19) E2A/pbx1 fusion protein. However, a combination of mAbs recognizing distinct epitopes can assure the detection of most if not all t(1;19)-derived E2A/pbx1 fusion proteins in t(1;19) childhood pre-B leukemias. Thus, a panel of well characterized mAbs recognizing distinct epitopes will be very useful for designing a t(1;19) pre-B leukemia-specific diagnostic kit which is based on the sensitive detection of the E2A/pbx1 fusion protein.

Serum-shed antigen

To determine if the E2A/pbx1 fusion protein is shed by ALL cells, culture supernatants from t(1;19) translocation-positive and negative cell lines are passively absorbed on plates. The selected antibodies can be screened for their ability to detect the antigen if it is shown that the antigen is shed. Combinations of mAbs can be used for a capture and detection assay. In a second phase, the assay can be refined using serial serum samples from archived patient material.

Production of Recombinant Monoclonal Antibodies

The present invention contemplates the production of recombinant monoclonal antibodies, and monoclonal antibody fragments such as Fab & $F_v$ fragments. Such monoclonal antibodies can be produced using recombinant DNA techniques that enable a skilled researcher to isolate the gene encoding the variavle region of the immunoglobulin light or heavy chains. The genes encoding variable region may then be molecularly manipulated to express those variable regions or part of the variable regions either alone or as part of a larger peptide. Typically, the variable region (or partial variable region) is expressed as part of an immunoglobulin molecule.

Preferably the antibody produced by the subject invention is heterodimeric and is therefore normally comprised of two different polypeptide chains, which together assume a conformation having a binding affinity, or association constant for the preselected antibody that is different, preferably higher, than the affinity or association constant of either of the polypeptides alone, i.e., as monomers. One or both of the different polypeptide chains is derived from the variable region of the light and heavy chains of an immunoglobulin. Typically, polypeptides comprising the light ($V_L$) and heavy ($V_H$) variable regions are employed together for binding the preselected antibody.

A $V_H$ or $V_L$ can be active in monomeric as well as multimeric forms, either homomeric or heteromeric, preferably heterodimeric. A $V_H$ and $V_L$ ligand binding polypeptide produced by the present invention can be advantageously combined in a heterodimer (antibody molecule) to modulate the activity of either or to produce an activity unique to the heterodimer. The individual ligand binding polypeptides will be referred to as $V_H$ and $V_L$ and the heterodimer will be referred to as an antibody molecule.

However, it should be understood that a $V_H$ binding polypeptide may contain in addition to the $V_H$, substantially all or a portion of the heavy chain constant region. A $V_L$ binding polypeptide may contain, in addition to the $V_L$, substantially all or a portion of the light chain constant region. A heterodimer comprised of a $V_H$ binding polypeptide containing a portion of the heavy chain constant region and a $V_L$ binding containing substantially all of the light chain constant region is termed a Fab fragment. The production of Fab can be advantageous in some situations because the additional constant region sequences contained in a Fab as compared to a $F_v$ could stabilize the $V_H$ and $V_L$ interaction. Such stabilization could cause the Fab to have higher affinity for antigen.

The individual $V_H$ and $V_L$ polypeptides will generally have fewer than 125 amino acid residues, more usually fewer than about 120 amino acid residues, while normally having greater than 60 amino acid residues, usually greater than about 95 amino acid residues, more usually greater than about 100 amino acid residues. Preferably, the $V_H$ will be from about 110 to about 125 amino acid residues in length while $V_L$ will be from about 95 to about 115 amino acid residues in length.

The amino acid residue sequences will vary widely, depending upon the particular idiotype involved. Usually, there will be at least two cysteines separated by from about 60 to 75 amino acid residues and joined by a disulfide bond.

In some situations, it is desirable to provide for covalent cross linking of the $V_H$ and $V_L$ polypeptides, which can be accomplished by providing cysteine residues at the carboxyl termini. The polypeptide will normally be prepared free of the immunoglobulin constant regions, however, a small portion of the J region may be included as a result of the advantageous selection of DNA synthesis primers. The D region will normally be included in the transcript of the $V_H$.

In other situations, it is desirable to provide a peptide linker to connect the $V_L$ and the $V_H$ to form a single-chain antigen-binding protein comprised of a $V_H$ and a $V_L$. This single-chain antigen-binding protein would be synthesized as a single protein chain. Such single-chain antigen-binding proteins have been described by Bird et al., *Science*, 242:423–426 (1988). The design of suitable peptide linker regions is described in U.S. Pat. No. 4,704,692 by Robert Landner.

Such a peptide linker could be designed as a part of the nucleic acid sequences contained in the expression vector. The nucleic acid sequences coding for the peptide linker would be between the $V_H$ and $V_L$ DNA homologs and the restriction endonuclease sites used to operatively link the $V_H$ and $V_L$ DNA homologs to the expression vector.

Typically the C terminus region of the $V_H$ and $V_L$ polypeptides will have a greater variety of the sequences than the N terminus and, based on the present strategy, can be further modified to permit a variation of the normally occurring $V_H$ and $V_L$ chains. A synthetic polynucleotide can be employed to vary one or more amino acids in a hypervariable region.

The following examples are intended to illustrate specific embodiments of the present invention. Those examples do not limit the scope of the invention claimed.

EXAMPLE 1

Fusion G199

An initial hybridoma fusion was carried out using splenocytes from the mice that were immunized with peptide 13

(fusion G199). Of the 2133 clones obtained, 10 were positive on the initial ELISA screen using the peptide 13. Seven of these clones were stable and could be analyzed for their reactivity with E2A, E2A/pbx1 fusion protein, pbx1, the carrier protein KHL and a control peptide (peptide 21) which carries the PDSYS (SEQ. ID. NO. 1) epitope of E2A but is missing the VLSIRGAQ (SEQ. ID. NO. 2) peptide of pbx. Analysis of the reactivity of the obtained monoclonal antibodies with these controls, indicated that all these antibodies reacted with an epitope that is present on E2A and is shared among the two peptides but absent on pbx1 (see Table 1). Thus, the epitope has to be the amino acid sequence PDSYS which turned out to be very immunogenic. In conclusion, none of the obtained monoclonal antibodies were E2A/pbx1 fusion protein specific.

TABLE 1

Reactivity of the G199 monoclonal antibodies with various proteins and peptides (using in-vitro translation for E2A, E2A/pbx1 and pbx1 or ELISA for pep13, pep21 and KLH). Abbreviations used: pep13 for peptide 13; pep21 for peptide 21; KLH for the carrier protein keyhole limpet hemocyanin. +++ symbolizes high reactivity, ++ medium reactivity, + low reactivity and no detectable reactivity.

| Clone | Reactivity with: | | | | | | Epitope: |
|---|---|---|---|---|---|---|---|
| | E2A | E2A/pbx1 | pbx1 | pep13 | pep21 | KLH | |
| G199-277 | + | + | − | + | ++ | − | PDSYS |
| G199-344 | + | + | − | + | + | − | PDSYS |
| G199-1265 | ++ | ++ | − | +++ | +++ | − | PDSYS |
| G199-1440 | + | + | − | ++ | ++ | − | PDSYS |
| G199-1514 | ++ | ++ | − | ++ | ++ | − | PDSYS |
| G199-1780 | + | + | − | ++ | ++ | − | PDSYS |
| G199-1867 | + | + | − | + | + | − | PDSYS |

EXAMPLE 2

Fusion G289

Since the PDSYS epitope was found to be highly immunogenic and an epitope has to be at least 5 amino acids, the peptide design was changed by deleting 2 amino acids from the N-terminus and adding 3 amino acids to the C-terminus. This strategy results in a loss of the immunogenic E2A epitope (PDSYS and maintains the fusion region SYSSVLSIR (SEQ. ID. NO. 9). A peptide was designed and synthesized composing the following amino acid residues: SYSVLSIRGAQEEC (peptide 14) (SEQ. ID. NO. 4). This sequence is based on the published sequence for the E2A/pbx1 junction region (Kamps M P, et al., *Cell* 60:547–555, 1990; Nourse J, et al. *Cell*, 60:535–545, 1990).

The last cystine residue was added to facilitate peptide conjugation to KLH using maleimide. The conjugated peptide was used as immunogen. Since initial attempts to raise monoclonal antibodies specific to the junction region based on conjugated peptide as the sole immunogen were not successful, purified recombinant GST fusion protein containing the E2A/pbx1 junction region (nt.1386–nt.1883) was subsequently used as antigen for the last two immunizations to enhance the possibility of developing specific antibodies. This junction-containing protein contained 20 amino acid residues from the E2A protein and 144 amino acid residues from pbx1. Balb/c mice were immunized with the modified peptide 14.

Out of 1000 hybridomas tested, 134 were positive by ELISA against KLH-peptide 14. Each of these 134 clones were subcloned by limiting dilution and selected for ELISA reactivity against KLH-peptide 14. To select antibodies recognizing the E2A/pbx1 junction only, these 134 clones were further tested for their reactivity to pbx1 and recombinant E2A/pbx1 junction proteins by dot blotting (Table 2).

TABLE 2

ELISA and dot blot reactivities of the G289 clones. The A, B, and C represented the reactivities to KLH conjugated peptide 14 by ELISA, to E2A/pbx1 junction protein by dot blot, and to pbx1 protein by dot blot correspondingly. The reactivity was shown in +++ as strong reactivity, ++ as medium reactivity, + as low reactivity, and − as no detectable reactivity.

| Clone G289- | Reactivity | | | Clone G289- | Reactivity | | | Clone G289- | Reactivity | | |
|---|---|---|---|---|---|---|---|---|---|---|---|
| | A | B | C | | A | B | C | | A | B | C |
| −52 | +++ | +++ | + | −2022 | +++ | +++ | + | −929 | +++ | +++ | − |
| −81 | +++ | +++ | ++ | −2023 | +++ | +++ | ++ | −1030 | +++ | +++ | ++ |
| −228 | +++ | +++ | ++ | −2069 | +++ | +++ | ++ | −1109 | +++ | +++ | − |
| −244 | +++ | +++ | ++ | −2078 | +++ | +++ | ++ | −1154 | +++ | +++ | + |
| −288 | +++ | +++ | +++ | −2085 | +++ | +++ | +++ | −1159 | +++ | +++ | − |
| −351 | +++ | +++ | ++ | −37 | +++ | +++ | − | −1186 | +++ | +++ | − |
| −356 | +++ | +++ | ++ | −40 | +++ | +++ | − | −1255 | +++ | +++ | − |
| −363 | +++ | +++ | ++ | −222 | +++ | +++ | ++ | −1256 | +++ | +++ | + |
| −438 | +++ | +++ | ++ | −423 | +++ | +++ | − | −1271 | +++ | +++ | + |
| −510 | +++ | +++ | +++ | −559 | +++ | +++ | − | −1357 | +++ | +++ | − |
| −535 | +++ | +++ | ++ | −1125 | +++ | +++ | + | −1373 | +++ | +++ | − |
| −607 | +++ | +++ | ++ | −1425 | +++ | +++ | − | −1414 | +++ | +++ | − |
| −626 | +++ | +++ | ++ | −1572 | +++ | +++ | ++ | −1441 | +++ | +++ | − |
| −635 | +++ | +++ | ++ | −1859 | +++ | +++ | ++ | −1490 | +++ | +++ | − |
| −661 | +++ | +++ | ++ | −1883 | +++ | +++ | ++ | −1521 | +++ | +++ | − |
| −663 | +++ | +++ | ++ | −1893 | +++ | +++ | − | −1550 | +++ | +++ | + |
| −695 | ++++ | +++ | − | −1988 | +++ | +++ | − | −1613 | ++++ | +++ | − |
| −726 | +++ | +++ | +++ | −2049 | +++ | +++ | − | −1645 | +++ | +++ | − |
| −761 | +++ | +++ | ++ | −2050 | +++ | +++ | + | −1682 | +++ | +++ | − |
| −763 | +++ | +++ | ++ | −2060 | +++ | +++ | ++ | −1704 | +++ | +++ | − |
| −911 | +++ | +++ | ++ | −1 | +++ | +++ | − | −1824 | +++ | +++ | − |
| −1080 | +++ | +++ | +++ | −50 | +++ | +++ | − | −1923 | +++ | +++ | + |
| −1144 | +++ | +++ | ++ | −90 | +++ | +++ | − | −1924 | +++ | +++ | − |
| −1305 | +++ | +++ | +++ | −211 | +++ | +++ | + | −1935 | +++ | +++ | + |

TABLE 2-continued

ELISA and dot blot reactivities of the G289 clones. The A, B, and C represented the reactivities to KLH conjugated peptide 14 by ELISA, to E2A/pbx1 junction protein by dot blot, and to pbx1 protein by dot blot correspondingly. The reactivity was shown in +++ as strong reactivity, ++ as medium reactivity, + as low reactivity, and − as no detectable reactivity.

| Clone G289- | Reactivity | | | Clone G289- | Reactivity | | | Clone G289- | Reactivity | | |
|---|---|---|---|---|---|---|---|---|---|---|---|
| | A | B | C | | A | B | C | | A | B | C |
| −1316 | +++ | +++ | +++ | −224 | +++ | +++ | − | −1951 | +++ | +++ | − |
| −1333 | +++ | +++ | ++ | −225 | +++ | +++ | + | −1960 | +++ | +++ | + |
| −1410 | +++ | +++ | ++ | −265 | +++ | +++ | + | −1964 | +++ | +++ | − |
| −1446 | +++ | +++ | +++ | −268 | +++ | +++ | − | −1974 | +++ | +++ | + |
| −1466 | +++ | +++ | + | −272 | +++ | +++ | − | −1984 | +++ | +++ | − |
| −1510 | ++++ | +++ | ++ | −283 | +++ | +++ | − | −1986 | +++ | +++ | − |
| −1525 | +++ | +++ | ++ | −310 | +++ | +++ | − | −1992 | +++ | +++ | − |
| −1582 | +++ | +++ | ++ | −312 | +++ | +++ | − | −1994 | +++ | +++ | − |
| −1618 | +++ | +++ | +++ | −353 | +++ | +++ | + | −2052 | +++ | +++ | − |
| −1729 | +++ | +++ | ++ | −384 | +++ | +++ | + | −2054 | +++ | +++ | − |
| −1758 | +++ | +++ | ++ | −406 | +++ | +++ | + | −2066 | +++ | +++ | ++ |
| −1771 | +++ | +++ | ++ | −441 | +++ | +++ | + | −2077 | +++ | +++ | + |
| −1776 | ++++ | +++ | ++ | −445 | +++ | +++ | − | −2087 | +++ | +++ | + |
| −1777 | +++ | +++ | + | −475 | +++ | +++ | − | −2088 | +++ | +++ | − |
| −1791 | +++ | +++ | ++ | −493 | +++ | +++ | + | | | | |
| −1865 | +++ | +++ | ++ | −521 | +++ | +++ | + | | | | |
| −1903 | +++ | +++ | ++ | −584 | +++ | +++ | + | | | | |
| −1957 | +++ | +++ | ++ | −613 | +++ | +++ | − | | | | |
| −1972 | +++ | +++ | ++ | −743 | +++ | +++ | − | | | | |
| −1973 | +++ | +++ | +++ | −694 | +'++ | +++ | − | | | | |
| −2002 | +++ | +++ | + | −703 | +++ | +++ | − | | | | |
| −2004 | +++ | +++ | ++ | −781 | +++ | +++ | − | | | | |
| −2016 | +++ | +++ | ++ | −887 | +++ | +++ | + | | | | |
| −2017 | '0 ++ | +++ | ++ | −913 | +++ | +++ | − | | | | |

All of the 134 clones were able to recognize the E2A/pbx1 junction protein. However, 22 clones failed to react with pbx1. These 22 clones, which do not interact with pbx1, were tested for reactivity with E2A/pbx1 but not with E2A from cell extract.

Figure 1B:
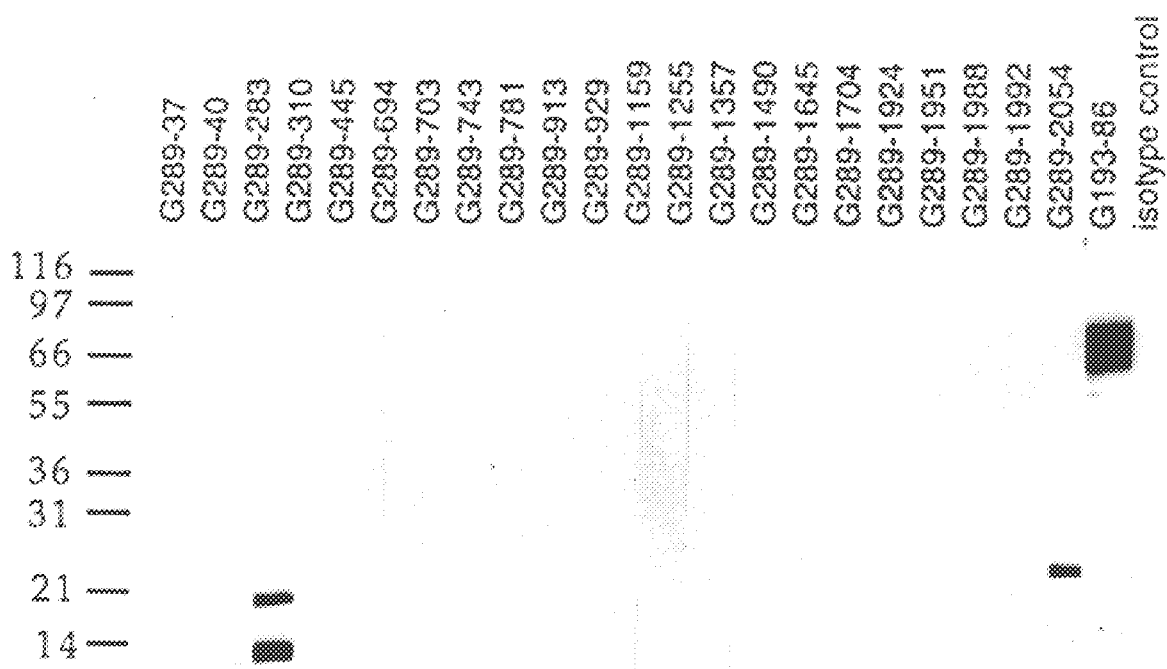

Cell lysate from the 697 pre-B cell line which contains the t(1;19) translocation, expresses the E2A/pbx1 protein was used for further evaluation of these 22 clones by western blotting. In addition, lysate from Namalwa cells, an EBV-transformed pre B line, which lacks expression of the E2A/pbx1 chimeric protein, was used as negative control. The results are shown in FIG. 1. The E2A-specific monoclonal antibody G193-86 (PharMingen) recognized a band of approximately 67 kD corresponding to the E2A protein in Namalwa cell lysate. In addition to the 67 kD band, an additional band of approximately 85 kD corresponding to E2A/pbx1 chimeric protein was recognized by G193-86 in the 697 cell lysate. All the G289 clones except G289-40 and G289-1159 recognize the E2A/pbx1 band in 697 cells. Clones G289-283, G289-310, G289-1357, G289-1704, and G289-2054 also recognized additional unidentified protein bands in 697 lysate. None of these reagents were capable of recognizing E2A in Namalwa cells. Similar results were obtained for the Jurkat T cell line (data not shown). The Jurkat cell line also fails to express the E2A/pbx1 chimeric protein. The 22 hybridoma clones neither recognized E2A nor pbx1 individually but did recognize the E2A/pbx1 chimeric protein. Peptide 14 was able to completely block monoclonal antibody reactivity to E2A/pbx1 with 697 cell lysate. The peptide 14 was not able to block the E2A-specific antibody G193-86 recognizing E2A/pbx1 and E2A.

In order to examine the specificity of these junction-specific monoclonal antibodies at a single cell level, the selected monoclonal antibodies were further characterized using immuno-staining and flow cytometric analysis. These junction-specific antibodies were purified by protein G sepharose chromatography and subsequently tested with an immunohistochemistry technique using a biotinylated polyclonal anti-mouse Ig followed by horse radish peroxidase-conjugated streptavidin. An anti-mouse IgG1 antibody as well as an anti-E12/E47 antibody were used as an isotype control and a positive staining antibody correspondingly. Distinct staining of 697 cell nuclei was observed for G289-781, and G289-1951 monoclonal antibodies. This result is consistent with published data that E2A/pbx1 is a nuclear localized protein (Kamps M P, et al. Genes Dev, 5:358–368, 1991; Jacobs Y, et al. Mol Cell Biol 13:7321–7333, 1993). None of the stained nuclei showed any nucleolar. It was noted that the intensity of staining of 697 cells varied between cells. This heterogeneity in staining did not change by increasing the antibody concentrations from 1 μg/μl to 40 μg/μl, although the intensity of the stained cells increased. There was no staining of the Namalwa cells or Jurkat cells by any of the tested E2A/pbx1 junction-specific antibodies.

The intracellular staining of E2A/pbx1 using junction-specific antibodies with 697 cells was also demonstrated by flow cytometry. An anti-mouse IgG1 antibody was used as isotype control. Over 95% of 697 cells were stained by the junction-specific antibodies compared with <5% Namalwa which was similar to that of the isotype negative control antibody. The fluorescence of stained cells was intracellular, as there was no staining observed by junction-specific antibodies when cells were not fixed and permeabilized prior to the addition of antibodies. Furthermore, preincubation of 1 ng of peptide 14 with the monoclonal antibodies was capable of blocking 697 cell staining. These combined results indicate that the 697 cell staining was E2A/pbx1-specific. The significant difference of staining between E2A/pbx1 positive and negative cells implies that these antibodies can also be used for flow cytometric studies. At equal concentration, the G289-781 clone showed the strongest fluorescence staining in comparison with the other 2 tested clones.

Using the monoclonal antibodies that are specific to the E2A/pbx1 fusion protein it was observed that there was heterogeneous staining of the t(1;19) containing 697 cells. A very small fraction of the cells were negative for the chimeric protein.

Additionally, there were positive staining cells with varying intensities. By using an IgM antibody that was specific to the fusion region (data not shown) and also by using varying concentrations of the IgG monoclonal antibodies it was noted that the intensity and not the frequency of the positive cells changed. It is not known whether the level of the E2A/pbx1 chimeric protein is regulated during the cell cycle, or whether this phenomena is due to clonal differences.

To test the diagnostic potential of G289-781 mAb, bone marrow specimens from four patients with leukemia were examined, without prior knowledge of the diagnosis based on cytogenetic analysis or immunophenotyping. Bone marrow samples of four patients with leukemia were obtained from the tissue bank of St. Jude Children's Research Hospital. The clinical and cytogenetic data of these four patients, designated 1, 2, 3, and 4, are summarized in Table 3.

It is possible to generate E2A/pbx1 fusion protein specific monoclonal antibodies by utilizing shorter versions of the junction region comprising the sequence YSVLS (SEQ. ID. NO. 11) or SVLS (SEQ. ID. NO. 12) (the underlined part of the peptides belong to the E2A protein and the bold part of the peptides belong to the pbx1 protein).

Two additional hybridoma fusions were carried out: (i) G193 using BALB/c mice that were immunized with a recombinant full-length E2A/pbx1 fusion protein expressed in Sf9 insect cells using a Baculovirus expression vector; and (ii) G197 using BALB/c mice immunized with peptide 21 (PDSYSDESVRSPGTFLSIRGC) (SEQ. ID. NO. 7).

EXAMPLE 3

Fusion G193

From 717 clones obtained, 11 were recognizing the E2A/pbx1 fusion protein and the epitope of 9 of them was localized in the E2A part (see Table 4). Only two of the clones (G193-365) were specific for the junction part or the E2A/pbx1 fusion protein when analyzed on Western blot using leukemia cell lysates. The clone G193-419 that recognized an epitope that was present on E2A and pbx1 and was not further characterized.

TABLE 3

Clinical and cytogenetic data of the four leukemia patients.

| Patient | Sex | Age | WBC | % Blasts | FAB | Immunotype | Cytogenetics |
|---|---|---|---|---|---|---|---|
| 1 | M | 11 yrs | 17,500 | 99 | L1 | Pre B ALL | t(1;19)(q23;p13) |
| 2 | M | 9 yrs | 12000 | 66 | L1 | Early Pre ALL | 57,XY [no t (1;19)] |
| 3 | F | 7 yrs | 36100 | 95 | L1 | Pre B ALL | 56,XX [no t (1;19)] |
| 4 | M | 8.5 yrs | 74100 | 95 | L1 | Pre B ALL | t(1;19)(q23;p13) |

Western blot analysis, flow cytometric analysis and immunohistochemical staining were carried out as previously described. Only specimens from patient 1 and 4 were positive for the E2A/pbx1 chimeric protein by western blotting, flow cytometry, and immunohisto chemistry. These results were found to be in exact agreement with the diagnosis based on cytogenetic analysis.

TABLE 4

Reactivity of the G193 monoclonal antibodies with various E2A and pbx1 containing recombinant proteins using ELISA and Western Blot. Abbreviations used: +++ symbolizes high reactivity, ++ medium reactivity, + low reactivity and − no detectable reactivity.

| | ELISA reactivity with: | | | Western blot reactivity with: | | | | |
|---|---|---|---|---|---|---|---|---|
| Clone | E2A | E2A/pbx1 | pbx1 | E2A | E2A/pbx1 | pbx1 | Epitope | Isotype |
| G193-11 | + | ++ | − | +− | − | | E2A | IgM, κ |
| G193-14 | +++ | +++ | − | −− | − | | E2A | IgM, κ |
| G193-51 | ++ | ++ | − | −++ | − | | E2A | IgG2a, λ |
| G193-86 | +++ | +++ | − | +++ | +++ | − | E2A | IgG1, λ |
| G193-328 | ++ | ++ | − | −− | − | | E2A | ? |
| G193-365 | − | +++ | − | −++ | − | | junction | IgG2b, λ |
| G193-371 | +++ | +++ | − | −− | − | | E2A | IgM, κ |
| G193-419 | +++ | +++ | ++ | ++ | ++ | + | ? | IgG1,λ |
| G193-450 | − | ++ | − | −+ | − | | junction | IgM, κ |
| G193-622 | +++ | +++ | − | −− | − | | E2A | IgM, κ |
| G193-633 | +++ | +++ | − | −− | − | | E2A | IgM, κ |

EXAMPLE 4

Fusion G197 (Splice variants)

Leukemias containing the t(1;19) translocation have been reported in which the fusion between E2A and pbx1 occurs at a different point from the predominately observed major junction position (Numata S-L Kato K, et al., supra). These variant junction fusion proteins may be the result of alternative splicing. Izraeli S, et al., supra reported a an E2A/pbx1 transcript with a variant junction containing a 27 base pair of an in-frame insertion.

From 1987 clones generated using peptide 21 as an immunogen, 12 clones were specifically recognizing peptide 21 in ELISA and did not crossreact with peptide 13 nor with the carrier protein KLH. From these 12 clones, 7 were minor variant E2A/pbx1 junction-specific (epitope:DSYSDESV) (SEQ. ID. NO. 5) (peptide 21) and did not see pbx1, the major junction form of E2A/pbx1 nor E2A (see Table 5). One clone (G197-1146) recognized an epitope of the splice insertion (DESVRSPGTF) (SEQ. ID. NO. 10) which is derived from an unknown origin in the genome and is not present on peptide 21, not on peptide 13, nor on E2A. The remaining 4 clones recognized the PDSYS epitope of E2A. Results are shown in Table 5.

TABLE 5

Reactivity of the G193 monoclonal antibodies with various E2A and pbx1 containing recombinant proteins using ELISA and Western Blot. Abbreviations used: +++ symbolizes high reactivity, ++ medium reactivity, + low reactivity and − no detectable reactivity.

ELISA reactivity with:

| Clone | E2A/pbx1 | pbx1 | pept13 | pept21 | KLH | Epitope: |
|---|---|---|---|---|---|---|
| G197-253 | − | − | − | +++ | − | DSYSDESV |
| G197-426 | − | − | − | + | − | DSYSDESV |
| G197-457 | − | − | − | +++ | − | DSYSDESV |
| G197-495 | − | − | − | +++ | − | DSYSDESV |
| G197-554 | − | − | − | +++ | − | DSYSDESV |
| G197-639 | − | − | − | +++ | − | DSYSDESV |
| G197-1146 | +++ | − | − | +++ | − | DESVRSPGTF |
| G197-1277 | + | − | − | +++ | − | PDSYS |
| G197-1325 | +++ | − | − | +++ | − | PDSYS |
| G197-1619 | +++ | − | − | +++ | − | PDSYS |
| G197-1713 | − | − | − | +++ | − | DSYSDESV |
| G197-1916 | +++ | − | − | +++ | − | PDSYS |

EXAMPLE 5

Production of monoclonal antibodies against the human pbx1 protein

Immunizations utilizing random fragments of the pbx1 protein resulted in no pbx1-specific hybridomas. This is a result of the low antigenicity of the pbx1 protein. Thus, it is necessary to utilize specific regions of the pbx1 protein.

The method used to produce the pbx1 specific mAbs is the same as that previously described for the production of the E2A/pbx1 specific mAbs except that the peptide sequence is different. Allignment of the sequence of pbx1, pbx2, and pbx3 proteins indicated that there are several regions past the E2A junction that are present in pbx1 and are not conserved in pbx2 and pbx3. These are regions 330–340, 410 and 420. A peptide immunogen corresponding to region 330–340 (amino acids 313 to 326 of pbx1), comprising at least 3 contiguous amino acids selected from the sequence ATNVSAHGSQANSP (SEQ. ID. NO. 6) can be used to produce mAb to pbx1. Examples of such contiguous amino acids include ATN, TNV, NVS, etc.

EXAMPLE 6

Detection of t(1:19) translocation using pbx1 specific mAbs

Preparation of cells and methods of detection are as previously described. It is necessary to include a B-cell marker to insure that positive cells that are scanned are of the B-cell lineage. Two color-staining is carried out, for example, utilizing direct conjugates of the pbx1 specific monoclonal antibody and the B-cell marker. Pan-B cell markers include the following:CD19, CD20, surface immunoglobulin, CD40, CD72, CD79a. It may also be useful to scan cells of T-cell lineage as these cells may also exhibit the relevant translocation. Pan T-cell markers include: CD5, CD7, CD3, αβTcR, and CD4/CD8 combination.

Other embodiments are within the following claims.

We claim:

1. A monoclonal antibody which specifically binds with an E2A/pbx1 fusion protein, wherein said monoclonal antibody specifically binds to the fusion junction between E2A and pbx1 comprising the sequence SYSVLS (SEQ. ID. NO. 3) and does not bind with an E2A peptide PDSYS (SEQ. ID. NO. 1).

2. A monoclonal antibody raised against an immunogenic fusion peptide comprising the sequence SYSVLS (SEQ. ID. NO. 3) and should said immunogenic fusion peptide have additional sequence located at the N-terminus of said sequence SYSVLS said additional sequence is not the sequence PD.

3. The monoclonal antibody of claim 2, wherein said immunogenic fusion peptide comprises SYSVLSIRGAQEEC (SEQ. ID. NO. 4) and should said immunogenic fusion peptide have additional sequence located at the N-terminus of said sequence SYSVLS said additional sequence is not the sequence PD.

4. The monoclonal antibody of claim 2, wherein said immunogenic fusion peptide is SYSVLSIRGAQEEC (SEQ. ID. NO. 4).

5. A monoclonal antibody raised against an immunogenic fusion peptide comprising the sequence YSVLS (SEQ. ID. NO. 11) and should said immunogenic fusion peptide have additional sequence located at the N-terminus of said sequence SYSVLS said additional sequence is not the sequence PD.

6. A monoclonal antibody raised against an immunogenic fusion peptide comprising the sequence SVLS (SEQ. ID. NO. 12) and should said immunogenic fusion peptide have additional sequence located at the N-terminus of said sequence SYSVLS said additional sequence is not the sequence PD.

7. Method of producing a monoclonal antibody which is immunospecific for a E2A/pbx1 fusion protein, wherein said monoclonal antibody specifically binds to the fusion junction between E2A and pbx1, comprising the steps of:

a) immunizing a mouse with a fusion peptide comprising the sequence SYSVLS (SEQ. ID. NO. 3) and should said immunogenic fusion peptide have additional sequence located at the N-terminus of said sequence SYSVLS said additional sequence is not the sequence PD;

b) producing a plurality of hybridoma cell lines from said mouse; and c) identifying among said plurality of hybridoma cell lines those which produce a monoclonal antibody which specifically reacts with said E2A/pbx1 fusion protein.

8. The method of claim 7, wherein said fusion peptide comprises the sequence SYSVLSIRGAQEEC (SEQ. ID. NO. 4) and should said immunogenic fusion peptide have additional sequence located at the N-terminus of said sequence SYSVLS said additional sequence is not the sequence PD.

9. The method of claim 7, wherein said fusion peptide has the sequence SYSVLSIRGAQEEC (SEO. ID. NO. 4).

10. Culturing said hybridoma cell lines of claim 7 which produce a monoclonal antibody which specifically reacts with said E2A/pbx1 fusion protein.

11. A hybridoma cell line which produces a monoclonal antibody which specifically reacts with an E2A/pbx1 fusion protein wherein said monoclonal antibody specifically binds to the fusion junction between E2A and pbx1 comprising the sequence SYSVLS (SEQ. ID. NO. 3) and does not bind with an E2A peptide PDSYS (SEQ. ID. NO. 1).

12. A hybridoma cell line which produces a monoclonal antibody which was made using a fusion peptide comprising the sequence SYSVLS (SEQ. ID. NO. 3) and should said immunogenic fusion peptide have additional sequence located at the N-terminus of said sequence SYSVLS said additional sequence is not the sequence PD.

13. A method for detecting a patient having acute lymphoblastic leukemia characterized by the presence of an E2A/pbx1 fusion protein, comprising the steps of:

a) contacting a sample obtained from a patient suspected of having acute lymphoblastic leukemia with a monoclonal antibody specifically reactive with said E2A/pbx1 fusion protein, wherein said monoclonal antibody specifically binds to the fusion junction between E2a and pbx1 and does not bind with an E2A peptide PDSYS (SEQ. ID. NO. 1) so as to form a detectable complex between said monoclonal antibody and said E2A/pbx1 fusion protein present in said sample; and b) detecting the presence of said complex as an indication of acute lymphoblastic leukemia in said patient.

14. The method of claim 13, wherein said monoclonal antibody is raised against a peptide comprising the sequence SYSVLS (SEQ. ID. NO. 3) and should said immunogenic fusion peptide have additional sequence located at the N-terminus of said sequence SYSVLS said additional sequence is not the sequence PD.

15. The method of claim 13, wherein the monoclonal antibody is raised against a peptide comprising the sequence SYSVLSIRGAQEEC (SEQ. ID. NO. 4) and should said immunogenic fusion peptide have additional sequence located at the N-terminus of said sequence SYSVLS said additional sequence is not the sequence PD.

16. The method of claim 13, wherein said monoclonal antibody is raised against a peptide with the sequence SYSVLSIRGAQEEC (SEQ. ID. NO. 4).

17. A method for detecting a patient having acute lymphoblastic leukemia characterized by the presence of an E2A/pbx1 fusion protein, comprising the steps of:
   a) individually contacting a sample obtained from a patient suspected of having acute lymphoblastic leukemia with each member of a panel of monoclonal antibodies specifically reactive with said E2A/pbx1 fusion protein and does not bind with an E2A peptide PDSYS (SEO. ID. NO. 1) so as to allow a detectable complex to form between a member of said panel of monoclonal antibodies and said E2A/pbx1 fusion protein present in said sample; and
   b) detecting the presence or absence of said complexes produced from said panel of monoclonal antibodies as an indication of the presence of acute lymphoblastic leukemia in said patient.

18. A kit for detecting acute lymphoblastic leukemia, said kit comprising one or more monoclonal antibody compositions comprising one or more monoclonal antibodies raised against a fusion peptide comprising the sequence SYSVLS (SEQ. ID. NO. 3) and should said immunogenic fusion peptide have additional sequence located at the N-terminus of said sequence SYSVLS said additional sequence is not the sequence PD and which specifically reacts with an E2A/pbx1 fusion epitope or E2A/pbx1 fusion protein.

19. The kit of claim 18, further comprising reagents useful for detecting one or more of said monoclonal antibodies.

20. A monoclonal antibody which specifically binds with an E2A/pbx1 fusion splice variant protein raised against an immunogenic fusion peptide comprising the sequence PDSYSDESVRSPGTFLSIRGC (SEQ. ID. NO. 7).

21. A hybridoma cell line which produces a monoclonal antibody which specifically binds to an E2A/pbx1 fusion splice variant protein and raised against an immunogenic fusion peptide comprising the sequence PDSYSDESVRSPGTFLSIRGC (SEQ. ID. NO. 7).

22. Method of producing a monoclonal antibody which is immunospecific for a E2A/pbx1 fusion splice variant protein, wherein said monoclonal antibody specifically binds to the fusion junction between E2A and pbx1, comprising the steps of:
   a) immunizing a mouse with a fusion peptide comprising the sequence PDSYSDESVRSPGTFLSIRGC (SEQ. ID. NO. 7);
   b) producing a plurality of hybridoma cell lines from said mouse; and
   c) identifying among said plurality of hybridoma cell lines those which produce a monoclonal antibody which specifically reacts with said E2A/pbx1 fusion protein.

23. Monoclonal antibodies or monoclonal antibody fragments produced using recombinant DNA techniques which specifically bind with an E2A/pbx1 fusion protein, wherein said monoclonal antibody specifically binds to the fusion junction between E2A and pbx1 and does not bind with an E2A peptide PDSYS (SEQ. ID. NO. 1).

24. A monoclonal antibody which specifically binds to pbx1 protein and does not bind with pbx2 or pbx3 protein and which was raised against an immunogenic peptide containing sequence that is not present in the pbx2 and pbx3 proteins.

25. A monoclonal antibody which specifically binds to pbx1 protein and does not bind with pbx2 or pbx3 protein raised against an immunogenic peptide comprising three or more contiguous amino acids selected from the sequence ATNVSAHGSQANSP (SEQ. ID. NO. 6).

26. Method of producing a monoclonal antibody which is immunospecific for pbx1 comprising the steps of:
   a) immunizing a mouse with a peptide comprising three or more contiguous amino acids selected from the sequence ATNVSAHGSQANSP (SEQ. ID. NO. 6);
   b) producing a plurality of hybridoma cells lines from said mouse; and
   c) identifying among said plurality of hybridoma cell lines those which produce a monoclonal antibody which specifically reacts with pbx1 protein and does not react with pbx2 or pbx3 protein.

27. Culturing said hybridoma cell lines of claim 26 which produce a monoclonal antibody which specifically reacts with said pbx1 protein and does not react with pbx2 or pbx3 protein.

28. A hybridoma cell line which produces a monoclonal antibody which specifically reacts with pbx1 protein and does not react with pbx2 or pbx3 protein and which was raised against an immunogenic peptide containing sequence that is not present in the pbx2 and pbx3 proteins.

29. A method for detecting a patient having acute lymphoblastic leukemia characterized by the presence of an E2A/pbx1 fusion protein, comprising the steps of:
   a) contacting a sample obtained from a patient suspected of having acute lymphoblastic leukemia with a monoclonal antibody specific for a pan-B cell surface antigen or a monoclonal antibody specific for a pan-T cell surface antigen,
   b) a monoclonal antibody specifically reactive with pbx1 so as to form a detectable complex between said monoclonal antibody and an E2A/pbx1 fusion protein present in said sample; and
   c) detecting the presence of said complex in cells of B or T cell lineage as an indication acute lymphoblastic leukemia in said patient.

30. A method for detecting a patient having acute lymphoblastic leukemia characterized by the presence of an E2A/pbx1 fusion protein, comprising the steps of:
   a) contacting a sample obtained from a patient suspected of having acute lymphoblastic leukemia with a monoclonal antibody specific for a pan-B cell surface antigen or a monoclonal antibody specific for a pan-T cell surface antigen,
   b) individually contacting said sample with each member of a panel of monoclonal antibodies specifically reactive with pbx1 protein so as to allow a detectable complex to form between a member of said panel of monoclonal antibodies and an E2A/pbx1 fusion protein present in said sample; and
   c) detecting the presence or absence of said complexes produced from said panel of monoclonal antibodies in cells of B or T cell lineage as an indication of the presence of acute lymphoblastic leukemia in said patient.

31. A kit for detecting acute lymphoblastic leukemia, said kit comprising one or more monoclonal antibody compositions comprising one or more monoclonal antibodies which specifically react with pbx1 and one or more monoclonal antibody compositions comprising one or more monoclonal antibodies which specifically react with a pan-B cell surface antigen or a pan-T cell surface antigen.

32. The kit of claim 31, further comprising reagents which detect one or more of said monoclonal antibodies.

33. Monoclonal antibodies or monoclonal antibody fragments produced using recombinant DNA techniques, which specifically bind pbx1 protein and does not bind pbx2 or pbx3 protein and which was raised against an immunogenic peptide containing sequence that is not present in the pbx2 and pbx3 proteins.

34. The method of claim 13, wherein said monoclonal is raised against an immunogenic fusion peptide comprising the sequence PDSYSDESVRSPGTFLSIRGC (SEQ. ID. NO. 7).

* * * * *

SEQUENCE LISTING ( 1 ) GENERAL INFORMATION:

( i i i ) NUMBER OF SEQUENCES: 12

( 2 ) INFORMATION FOR SEQ ID NO: 1:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 1:

Pro  Asp  Ser  Tyr  Ser
1                             5

( 2 ) INFORMATION FOR SEQ ID NO: 2:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 2:

```
Val  Leu  Ser  Ile  Arg  Gly  Ala  Gln
 1                    5
```

( 2 ) INFORMATION FOR SEQ ID NO: 3:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 3:

```
Ser  Tyr  Ser  Val  Leu  Ser
 1                    5
```

( 2 ) INFORMATION FOR SEQ ID NO: 4:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 4:

```
Ser  Tyr  Ser  Val  Leu  Ser  Ile  Arg  Gly  Ala  Gln  Glu  Glu  Cys
 1                    5                          10
```

( 2 ) INFORMATION FOR SEQ ID NO: 5:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 5:

```
Asp  Ser  Tyr  Ser  Asp  Glu  Ser  Val
 1                    5
```

( 2 ) INFORMATION FOR SEQ ID NO: 6:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 6:

```
Ala  Thr  Asn  Val  Ser  Ala  His  Gly  Ser  Gln  Ala  Asn  Ser  Pro
 1                    5                          10
```

( 2 ) INFORMATION FOR SEQ ID NO: 7:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 7:

```
Pro  Asp  Ser  Tyr  Ser  Asp  Glu  Ser  Val  Arg  Ser  Pro  Gly  Thr  Phe
 1              5                        10                            15
Leu  Ser  Ile  Arg  Gly  Cys
                 20
```

( 2 ) INFORMATION FOR SEQ ID NO: 8:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 8:

```
Pro  Asp  Ser  Tyr  Ser  Val  Leu  Ser  Ile  Arg  Gly  Ala  Gln
 1              5                        10
```

( 2 ) INFORMATION FOR SEQ ID NO: 9:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 9:

```
Ser  Tyr  Ser  Ser  Val  Leu  Ser  Ile  Arg
 1              5
```

( 2 ) INFORMATION FOR SEQ ID NO: 10:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 10:

```
Asp  Glu  Ser  Val  Arg  Ser  Pro  Gly  Thr  Phe
 1              5                          10
```

( 2 ) INFORMATION FOR SEQ ID NO: 11:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 11:

-continued

Tyr Ser Val Leu Ser
1               5

(2) INFORMATION FOR SEQ ID NO: 12:

(i) SEQUENCE CHARACTERISTICS:
      (A) LENGTH: 4 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 12:

Ser Val Leu Ser
1